US009798862B2

(12) United States Patent
Parviainen

(10) Patent No.: US 9,798,862 B2
(45) Date of Patent: Oct. 24, 2017

(54) APPARATUS FOR DISPENSING MEDICINE, VITAMINS AND/OR SAMPLES

(71) Applicant: NEWICO OY, Kuopio (FI)

(72) Inventor: Ossi Parviainen, Kuopio (FI)

(73) Assignee: NEWICO OY, Kuopio (FI)

( * ) Notice: Subject to any disclaimer, the term of this patent is extended or adjusted under 35 U.S.C. 154(b) by 0 days.

(21) Appl. No.: 14/362,246

(22) PCT Filed: Nov. 28, 2012

(86) PCT No.: PCT/FI2012/051176
§ 371 (c)(1),
(2) Date: Jun. 2, 2014

(87) PCT Pub. No.: WO2013/079792
PCT Pub. Date: Jun. 6, 2013

(65) Prior Publication Data
US 2014/0371904 A1      Dec. 18, 2014

(30) Foreign Application Priority Data

Dec. 2, 2011  (FI) ..................................... 20116223

(51) Int. Cl.
*G06F 19/00*    (2011.01)
*G07F 17/00*    (2006.01)
(Continued)

(52) U.S. Cl.
CPC ............ *G06F 19/3462* (2013.01); *A61J 1/03* (2013.01); *A61J 7/0069* (2013.01); *A61J 7/0092* (2013.01);
(Continued)

(58) Field of Classification Search
CPC ....... A61J 7/0069; A61J 1/03; G06F 19/3462; G07F 17/0092
(Continued)

(56) References Cited

U.S. PATENT DOCUMENTS

| 5,661,978 A * | 9/1997 | Holmes ................... F25B 21/02 |
| | | 312/209 |
| 5,710,551 A * | 1/1998 | Ridgeway ............. A61J 7/0084 |
| | | 128/920 |

(Continued)

FOREIGN PATENT DOCUMENTS

| EP | 2 082 718 A2 | 7/2009 |
| NO | 2008/086628 A1 | 7/2008 |

(Continued)

OTHER PUBLICATIONS

International Search Report issued in International Patent Application No. PCT/FI2012/051176 mailed Mar. 21, 2013.

(Continued)

*Primary Examiner* — Michael K Collins
(74) *Attorney, Agent, or Firm* — Oliff PLC

(57) ABSTRACT

An apparatus for distributing medicines, vitamins and/or samples, including an organizer and dispensing units for medicines, vitamins and/or samples. The organizer includes seats in which to place the dispensing units. The apparatus includes an identification device connected to a data processing device and containing dispensing data on medicines, vitamins and/or samples, including detecting members controlled to a detecting state by detecting signals generated on the basis of dispensing data in the data processing device. The identification device is configured to be brought in connection with the organizer so that at least some of the detecting members are aligned with at least some of the seats of the organizer, wherein at least those dispensing units, which are aligned with at least one detecting member, can be identified by means of detecting signals generated on the basis of dispensing data in the data processing device.

8 Claims, 3 Drawing Sheets

(51) Int. Cl.
*A61J 1/03* (2006.01)
*A61J 7/00* (2006.01)
*B01L 9/06* (2006.01)
*B01L 3/00* (2006.01)
*A61B 5/15* (2006.01)

(52) U.S. Cl.
CPC *B01L 3/54* (2013.01); *B01L 9/06* (2013.01); *G07F 17/0092* (2013.01); *A61B 5/150343* (2013.01); *B01L 2300/021* (2013.01); *B01L 2300/022* (2013.01)

(58) Field of Classification Search
USPC .................................................. 700/236, 242
See application file for complete search history.

(56) References Cited

U.S. PATENT DOCUMENTS

| | | | |
|---|---|---|---|
| 5,883,806 A | 3/1999 | Meador et al. | |
| 6,116,461 A * | 9/2000 | Broadfield | A61G 12/001 206/443 |
| 6,138,865 A * | 10/2000 | Gilmore | A61J 7/0084 221/2 |
| 6,294,999 B1 * | 9/2001 | Yarin et al. | 340/573.1 |
| 6,529,446 B1 * | 3/2003 | de la Huerga | A61J 7/0084 368/10 |
| 7,369,919 B2 * | 5/2008 | Vonk et al. | 700/236 |
| 7,801,745 B2 * | 9/2010 | Walker | G06F 19/3462 221/125 |
| 7,854,326 B1 | 12/2010 | Beckett | |
| 8,085,135 B2 * | 12/2011 | Cohen Alloro et al. | 340/309.16 |
| 8,193,918 B1 * | 6/2012 | Shavelsky | A61J 7/04 340/309.16 |
| 8,380,346 B2 * | 2/2013 | Chudy et al. | 700/242 |
| 8,670,865 B2 * | 3/2014 | Coe | A61J 7/0481 700/232 |
| 8,700,212 B1 * | 4/2014 | Bruno et al. | 700/242 |
| 9,233,051 B2 * | 1/2016 | Tufi | A61J 1/035 |
| 9,355,218 B2 * | 5/2016 | Brown | A61J 7/0084 |
| 2002/0032582 A1 | 3/2002 | Feeney et al. | |
| 2005/0162979 A1 * | 7/2005 | Ostergaard | A61J 1/035 368/10 |
| 2006/0058917 A1 * | 3/2006 | Vonk et al. | 700/236 |
| 2008/0300719 A1 * | 12/2008 | Duke | A61J 7/0481 700/244 |
| 2009/0152291 A1 * | 6/2009 | Ohmura et al. | 221/197 |
| 2009/0281657 A1 * | 11/2009 | Gak | A61J 7/0481 700/242 |
| 2009/0301925 A1 * | 12/2009 | Alloro | A61J 7/0409 206/534 |
| 2010/0256808 A1 * | 10/2010 | Hui | G07F 7/025 700/225 |
| 2010/0305749 A1 * | 12/2010 | Coe | A61J 7/0481 700/231 |
| 2011/0004338 A1 * | 1/2011 | Bianco | G07F 11/62 700/235 |
| 2011/0060457 A1 * | 3/2011 | De Vrught | A61J 1/03 700/241 |
| 2013/0024022 A1 * | 1/2013 | Bowers | A61J 1/03 700/236 |

FOREIGN PATENT DOCUMENTS

| | | |
|---|---|---|
| NO | 2011/064600 A1 | 6/2011 |
| WO | 02/17850 A1 | 3/2002 |
| WO | 2006/086735 A3 | 3/2007 |
| WO | WO 2010/120241 A1 | 10/2010 |

OTHER PUBLICATIONS

Written Opinion of the International Searching Authority issued in International Patent Application No. PCT/FI2012/051176 mailed Mar. 21, 2013.
International Preliminary Report on Patentability issued in International Patent Application No. PCT/FI2012/051176 mailed Nov. 13, 2013.
Office Action issued in Finnish Patent Application No. 20116223 dated Aug. 2, 2012 (with translation).
Office Action issued in Finnish Patent Application No. 20116223 dated Nov. 29, 2013 (with translation).
Oct. 4, 2016 Office Action issued in Russian Patent Application No. 2014126813.
Jun. 25, 2015 Search Report issued in European Patent Application No. 12853366.8.
Dietz, Paul, et al. "Very Low-Cost Sensing and Communication Using Bidirectional LEDs". Technical Report Mitsubishi Electric Research Labratories. No. 2003-35, pp. 1-19, 2003.
Jun. 20, 2017 Office Action issued in Israeli Patent Application No. 232610.
Jul. 27, 2017 Notice of Allowance issued in Russian Patent Application No. 2014126813.

* cited by examiner

APPARATUS FOR DISPENSING MEDICINE, VITAMINS AND/OR SAMPLES

FIELD OF THE INVENTION

The invention relates to an apparatus for dispensing medicines, vitamins and/or samples.

BACKGROUND OF THE INVENTION

Medicines to be dispensed to patients at hospitals and health centres are usually administered 1 to 7 times a day. The dosing is performed in such a way that the dispensing nurse retrieves the data and doses of the medicines to be dispensed to each patient from a patient data register, and doses them in dispensing units to be placed ready on a tray or medicine organizer. The same medicine organizer or tray may contain the medicines for several patients, for example in such a way that the medicines for the patients in the same patient room or the medicines for the patients with the same disease in the same department for one or several days are dispensed on a single medicine organizer or tray. In each organizer, the medicines are dosed in such a way that the medicines for one patient are usually divided into different dispensing units according to their time of administration. In other words, a single medicine organizer or tray may contain dozens of medicine doses, and therefore the dispensing units have to be clearly marked with the person for whom the medicines in each dispensing unit are intended, and the time when they are to be administered to this patient. At present, the dispensing units are identified in such a way that the dispensing nurse writes or prints out an identification tag or label provided with the patient's name and data when the medicines in said dispensing unit have to be administered to the patient, and attaches said tag or label to each dispensing unit. After the dispensing, the ready dispensed medicine organizers or trays are often transferred to a marked place (e.g. a shelf on a locked cabinet) in a dispensing room, marked with e.g. the number of the department or room where the medicines dispensed on said medicine organizer or tray are intended to be delivered.

A drawback in the present method is that the dosage and dispensing of the medicines is performed entirely manually, wherein in spite of double checking there exists the possibility that the medicines dispensed in the dispensing units are not the medicines which were intended to be dispensed, or that the dispensing units to be administered are confused because of a human error at some stage. The same procedure is followed when dispensing vitamins to be administered to patients, and samples or sample units taken from patients, so that there is also a risk of confusion because of a human error in the storage or delivery of vitamins to be administered or samples to be taken.

BRIEF SUMMARY OF THE INVENTION

It is an aim of the invention to introduce a novel apparatus for dispensing medicines, vitamins and samples, for making the dosage to dispensing units, the identification of the dispensing units, as well as the administration to patients more reliable and safer than before. Furthermore, it is an aim of the invention to introduce an apparatus, by which the dosage and/or dispensing of medicines, vitamins and samples can be performed in a completely paperless way so that in the handling of the dispensing units, it is no longer necessary to print out and attach patient data tags to the dispensing units, for example for identifying them at the stage of administration.

The aim of the invention is achieved by an apparatus comprising an organizer for dispensing units, having organizer seats, in which dispensing units remain in place in such a way that they cannot be confused at any stage; as well as a separate identification device equipped with electronic detection means, by which the dispensing units placed on the organizer can be identified at any stage of dosing and dispensing, by placing the organizer in connection with the identification device in a specific way so that each dispensing unit in the organizer is always aligned with at least one and the same detector of the identification device, wherein each dispensing unit placed in the organizer at the dispensing stage can be identified by connecting the identification device to a data processing device that contains the dispensing data, wherein the identification device indicates the position of the dispensing unit for the medicine, vitamin and/or sample selected from the data processing device, on the organizer. More precisely, the apparatus according to the invention is characterized in what will be presented in the characterizing part of claim 1.

The apparatus according to the invention has the advantage that thanks to it, the risk of a human error in the dispensing of medicines, vitamins and samples can be made smaller than before. Furthermore, thanks to the apparatus according to the invention, the dispensing of medicines, vitamins and samples can be implemented without the use of identification tags, wherein the dispensing can be arranged in a completely paperless way, which, in turn, reduces the use of paper and the work and costs caused by it in e.g. hospitals and health centres.

DESCRIPTION OF THE DRAWINGS

In the following, the invention will be described in more detail with reference to the appended drawings, in which.

DETAILED DESCRIPTION OF THE INVENTION

Figure 1:
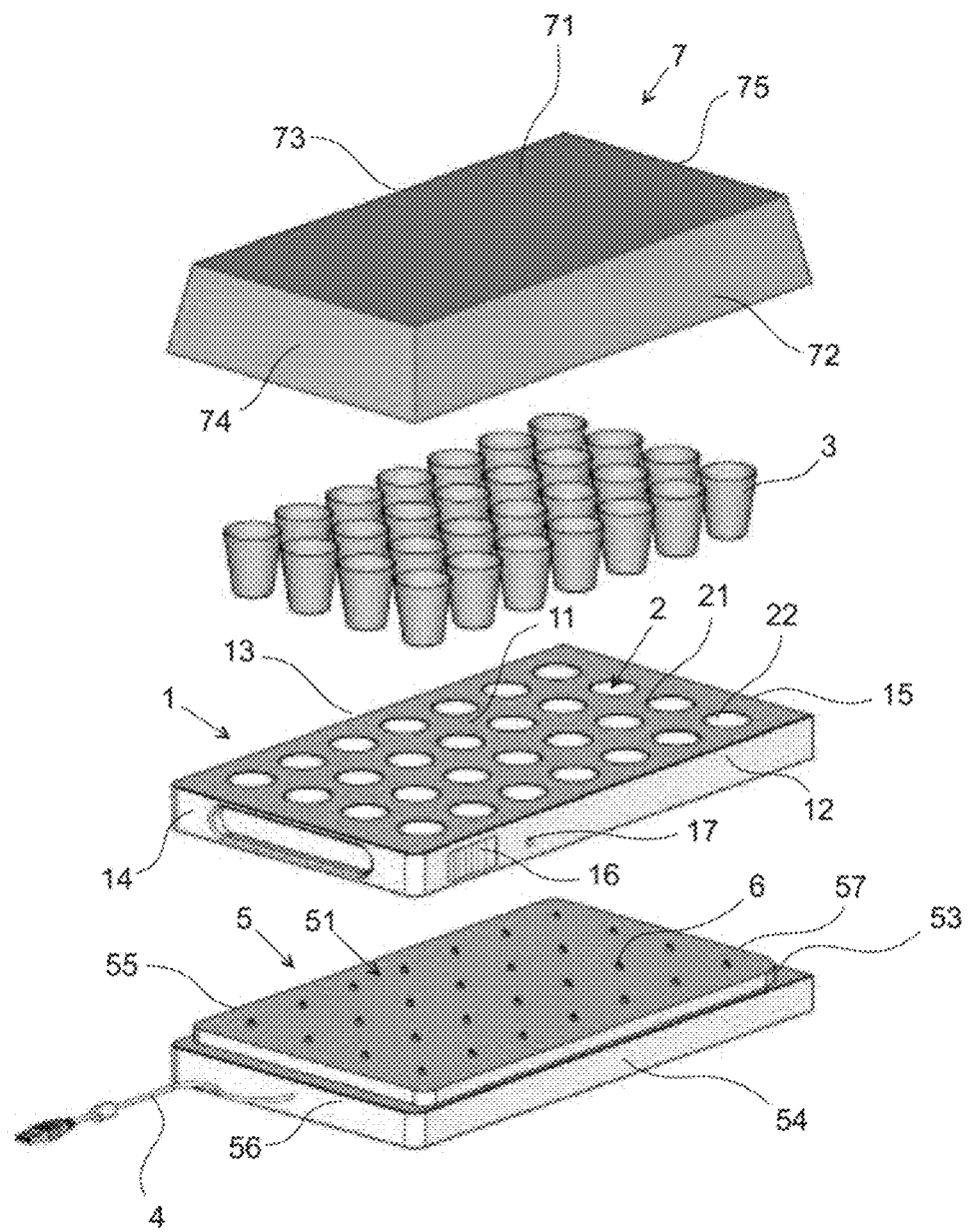
FIG. 1 shows parts of an apparatus according to the invention, separated from each other, in a slanted view from the side.

The apparatus shown in FIG. 1 comprises an organizer 1 with organizer seats 2 and dispensing units 3 to be placed in them, as well as an identification device 5 which is connected by a coupling means 4 to a data processing device that contains data on dispensing of medicines, vitamins and/or samples, and which comprises detectors 6 that can be controlled on the basis of dispensing data in the data processing device. Furthermore, the apparatus shown in FIG. 1 comprises a lid 7 to be placed on top of the organizer 1. In the apparatus according to FIG. 1, the organizer 1 can be placed on top of the identification device 5, and the lid 7 can be fastened and locked on top of the organizer 1. The embodiment of the apparatus shown in FIG. 1 is designed for the dispensing of pills of medicine and vitamins, but in principle, it could also be used for the dispensing of e.g. liquid medicine (such as cough mixture or the like).

Figure 2:
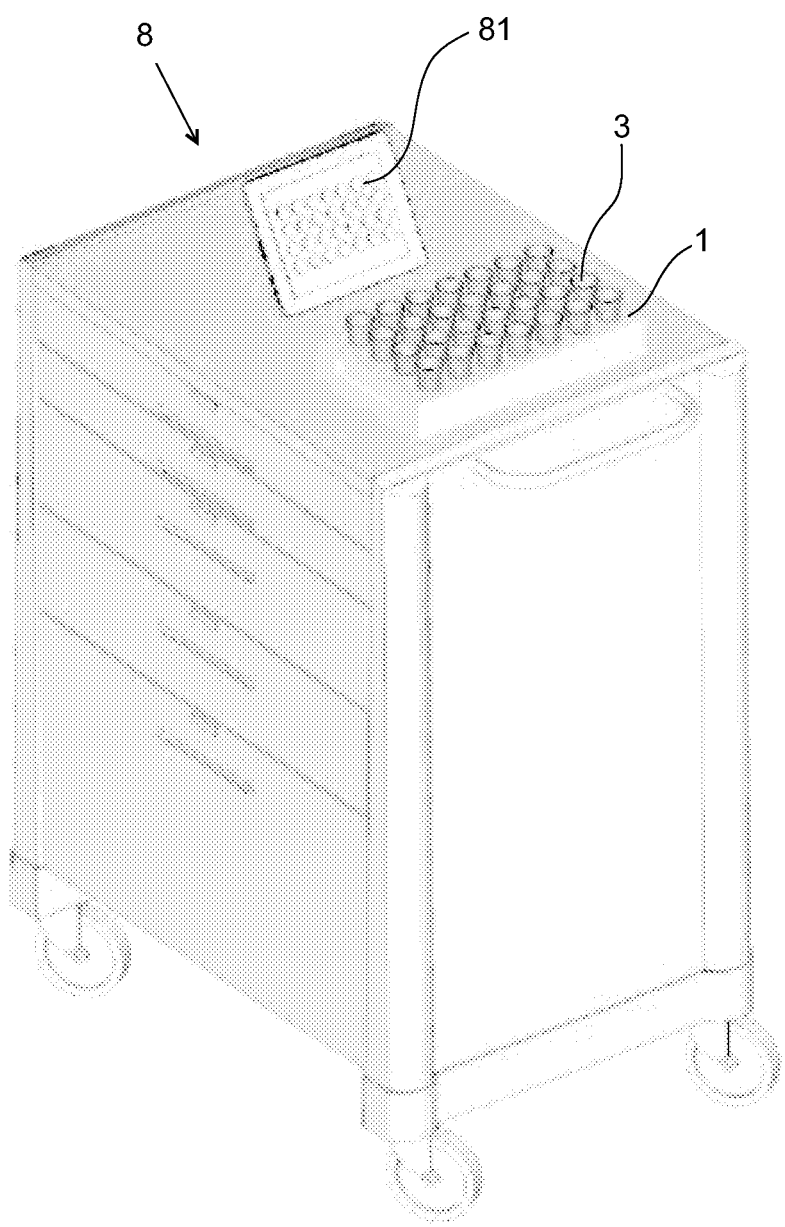
FIG. 2 shows a delivery cart suitable for the transportation of an organizer belonging to the apparatus, in a slanted view from above.

In the embodiment according to FIG. 1, the organizer 1 is a housing-like piece designed in the way shown in FIGS. 1 and 2, open from below (seen from the direction of FIG. 1), having a primarily flat plate-like upper wall 11, a first side wall 12 and a second side wall 13, as well as a first end wall 14 and a second end wall 15. The organizer seats 2 are circular openings 21 formed in the upper wall 11, all equal in size. The organizer of FIG. 1 has 28 seats. In this embodiment, the seats have conical supporting sleeves 22 which extend downwards from the mouth of the openings 21, that is, parallel to the side walls of the organizer 1. However, the supporting sleeves 22 are substantially shorter than the height of the side walls 12 and 13 and the end walls 14 and 15 in the vertical direction, wherein they do not touch the identification device 5 when the organizer 1 is placed on top of the identification device 5. The function of the supporting sleeves 22 is not only to hold the dispensing units in place but also to conduct light from the detecting members 6 of the identification device 5 to the sides of the dispensing units 2. The first side wall 12 of the organizer of FIG. 1 is provided with an identification tag 16 which, in this embodiment, is a bar code for identifying the organizer 1. Furthermore, the first side wall 12 of the organizer is also provided with an organizer tag 17 which, in this case, is an RFID tag, on the basis of which the identification device 5 identifies the organizer 1 and makes sure that it is placed the right way around with respect to the identification device 5.

In this case, the identification device 5 is a plate-like piece which is at least partly hollow inside, having an upper surface 51, a first side edge 54, a second side edge 55, a first end edge 56 and a second end edge 57. In the central parts of the top surface 51, there is a fitting portion 52 extending upwards from the other parts, and a supporting surface 53 around the same, to which surface the lower edges of the side walls 12 and 13 and the end walls 14 and 15 of the organizer 1 are supported when the organizer 1 is placed on top of the identification device 5. Detecting members 6 extending upwards from the upper surface 51 are provided at regular intervals at the adapter part 52. The detecting members 6 are in this case light emitting diodes (LED), and their number is 28, i.e. the same as the number of seats 2 in the organizer 1. The detecting members 6 are placed in such a way that they are aligned with the seats 2 in the organizer 1 when the organizer 1 is placed on top of the identification device 5. As to its outer dimensions, the adapter part 52 fits within the side edges 12 and 13 and the end edges 13 and 14 of the organizer 1 in a relatively clearance-free but sensitive way, wherein the organizer 1 placed on top of the identification device 5 cannot move in the direction of the plane formed by its upper wall 11 (that is, horizontally when on a horizontal base) nor vertically in the direction of the identification device 5 when it is fitted in the adapter part 52 of the identification device. In this embodiment, the coupling means 4 of the identification device is a USB cable placed at the first end 54 of the identification device. Furthermore, inside the identification device there is an organizer reader in the immediate vicinity of the first side edge, in this embodiment an RFID reader (in the immediate vicinity of the first side edge 54, at a position corresponding to the organizer tag 17 on the first side edge of the organizer), as well as an electronic control unit (an integrated circuit) which changes the state of the detecting members 6, that is, turns the light emitting diodes used as the detecting members 6 on and off according to the controls received by it. It should be noted that the control unit is also such that it simultaneously measures the voltage from the light emitting diodes (that is, the light received by the light emitting diodes), i.e. it is in that way capable of determining whether dispensing units 3 have been placed in the seats 2 or not.

In this case, the dispensing units 3 are cups which are open at the top, have a circular cross-section, and are in this case made of a material that is at least partly transparent to visible light (for example, plastic). The dispensing units 3 are all equal in size and conical in such a way that their diameter at the mouth 31 is greater than the diameter of the openings 21 of the seats 2, but the diameter at their bottom 32 is clearly smaller than the diameter of the openings 21 of the seats 2 and slightly smaller than the diameter of the lower end of the support sleeves of the seats 2 in such a way that when the organizer 3 is placed in the seat 2 of the organizer 2, it is supported by the supporting sleeve 22 in such a way that its bottom does not quite touch the detecting member 6 of the identification device 5 when the organizer 1 is placed on the identification device 5.

The lid 7 of the device is a box-like piece which is open from below and has an upper wall 71 as well as a first side wall 72, a second side wall 73, a first end wall 74, and a second end wall 75. Furthermore, the lid 7 comprises a locking device based on a key lock, a system lock or an electric lock (not shown in the figures) and comprising locking means which engage corresponding locking means in the organizer 1, by which locking means the lid can be locked on top of the upper wall 51 of the organizer and the dispensing units 2 placed in it so that the dispensing units or the medicines or vitamins dosed in them cannot be removed or confused without opening the locking of the lid 7. When the lock is placed on top of the organizer 1, its side walls 72 and 73 and end walls 74 and 75 are aligned with the side walls 12 and 13 and end walls 14 and 15 of the organizer, at the edges of the upper wall 11. In this case, the side walls 72 and 73 and the end walls 74 and 75 of the lid 7 have such a height that when the lid is placed on top of the organizer, it simultaneously closes the dispensing units 3 placed in the seats 2 of the organizer 1 in such a way that the medicines or vitamins in them cannot escape the dispensing units 3 even if the organizer 1 were turned upside down, if the medicines or vitamins are solid pieces (for example, pills). The lid 7 can also be hinged to the organizer 1.

When the apparatus according to FIG. 1 is used for dispensing medicines and/or vitamins in, for example, a hospital, the dispensing room contains a storage with a required number of organizers 1 and dispensing units 3 to be placed in them, as well as at least one identification device 5 connected to a data processing device that contains the dispensing data, and a bar code reader also connected to said data processing device. The medicines are dosed in such a way that the dispensing nurse (or other person responsible for the dispensing of medicines and/or vitamins) takes one organizer 1 from the organizer storage and reads the bar code 16 on its first side edge 12. The nurse then places the organizer 1 on top of the identification device 5 (wherein the organizer reader of the identification device detects on the basis of the tag 17 of the organizer 1 that the same organizer 1 has now been placed onto the identification device 5) and selects the data of the first medicine (or vitamin) to be dosed on said organizer 1 (for example, by means of the keyboard, mouse or touch screen of the data processing device). Thus, the data system controls the identification device 5 in such a way that it transmits a signal (i.e. voltage) to those detecting members 6, at which the dispensing units to be dispensed have to be placed, wherein the detecting members 6 are set to the detecting state, i.e. are lit. Next, the nurse takes a package of medicine to be dosed from the medicine chest, and makes sure that the package of medicine is correct by reading the bar code on the package with the bar code reader; if the package is incorrect, the data processing device will give a sound alarm and request to replace the package. After the nurse has made sure that the package of medicine is correct, he/she takes a required number of dispensing units 3 from the dispensing unit storage and doses medicine and/or vitamins from said package in a quantity displayed on the screen of the data processing device. After the dosage, the nurse places the dispensing units 3 on the organizer 1. Thus, the detection signals at the seats 2 intended for them are cut out, and the detecting members 6 are turned off the detecting state (i.e. the light emitting diodes go out) as dispensing units 3 are placed on the organizer 1, because the control unit of the identification device 5 detects that the dosed dispensing units are placed in the seats 2 according to the change in the quantity of light coming to the detecting members 6. Next, the nurse selects the next medicine to be dosed, wherein the procedure is started by using the bar code reader to read the bar code of the next package of medication displayed on the screen of the data processing device, after which the identification device 5 lights those detecting members 6, at which the next medicine is to be dispensed in the dispensing units 3 in the respective seats 2. After dosing in the above-mentioned way, the nurse places the dispensing units 3 in the seats 2 shown by the detecting members 6, wherein the detecting members 6 at the seats 2 for this medicine go out. From now on, the dosing is continued by repeating the above-described steps as long as all the seats 2 of the organizer are filled; after the last medicine for this organizer 1, the data system indicates that all the medicines intended for this organizer 1 have now been dosed. If it is not intended to dispense (=place dispensed dispensing units 3 in) all the seats of the organizer 1, the data system indicates after the last medicine/vitamin to be dosed that it is not intended to dispense any more on said organizer 1.

After the dispensing, the lid 7 on the organizer 1 is locked, and the organizer is placed in a storage compartment intended for it (e.g. a rack, a chest, or the like) to wait for dispensing of the medicines to patients, or if the dispensing is to be started at once, the organizer is placed on a delivery cart 8 (shown in FIG. 2) for transportation to the place of administration.

The administration of the dispensed medicines/vitamins can be performed, for example, in such a way that the ready dispensed organizer 1 is placed on an identification device 5 in the delivery cart 8, and is connected by a connecting means 4 to a data processing device that contains the dispensing data and is arranged in connection with the delivery cart 8. The data processing device of the delivery cart 8 is provided with a display 81 (for example, a touch screen), on which the address of the organizer (e.g. the hospital department and number or room where the medicines/vitamins are intended to be dispensed) is first displayed, when the organizer 1 is placed on top of the identification device 5. After this, the nurse moves the delivery cart 8 to the place determined by the address, where the administration of medicines and/or vitamins is to be started. At the place determined by the address, the patient is identified by reading, for example, a bar code attached e.g. to the edge of the bed or to a wristband worn by the patient, by a bar code reader provided in the delivery cart 8 and connected to the data processing device of the delivery cart 8. Thus, the data processing device gives the control unit a command to form a detecting signal, i.e. to light that or those detecting members 6 of the identification device 5, at which the dispensing units 3 contain the medicines intended to be administered to said identified patient at this administration time. After the nurse has administered the medicines, he/she acknowledges on the touch screen of the data processing device the medicines as having been administered, wherein the detecting members 6 go out. Alternatively or in addition, the detecting members 6 can be arranged to also go out on the basis that the dispensing unit(s) 3 has (have) been removed from said seat(s) 2. Now, the nurse moves the delivery cart 8 to the next patient and reads his/her bar code, whereby the identification device 5 lights the detecting members 6 at the medicine intended for this patient, so that the nurse will again know which medicines/vitamins contained in the dispensing unit(s) are to be administered to said patient. The nurse can continue the administration further as long as medicines/vitamins are left in said organizer 1. Naturally, several organizers 1 can be carried in the delivery cart 8. Thus, the preceding organizer 1 can be replaced with the next organizer 1 by locking the lid 7 of the preceding organizer 1 (at least if unadministered medicines/vitamins were left in the preceding organizer) and by moving this organizer 1 off the identification device into a compartment intended for organizers 1 in the delivery cart 8, and by placing the next organizer 1 on top of the identification device 5, to be detected by the organizer reader of the identification device 5 on the basis of the organizer tag 17.

Figure 3:
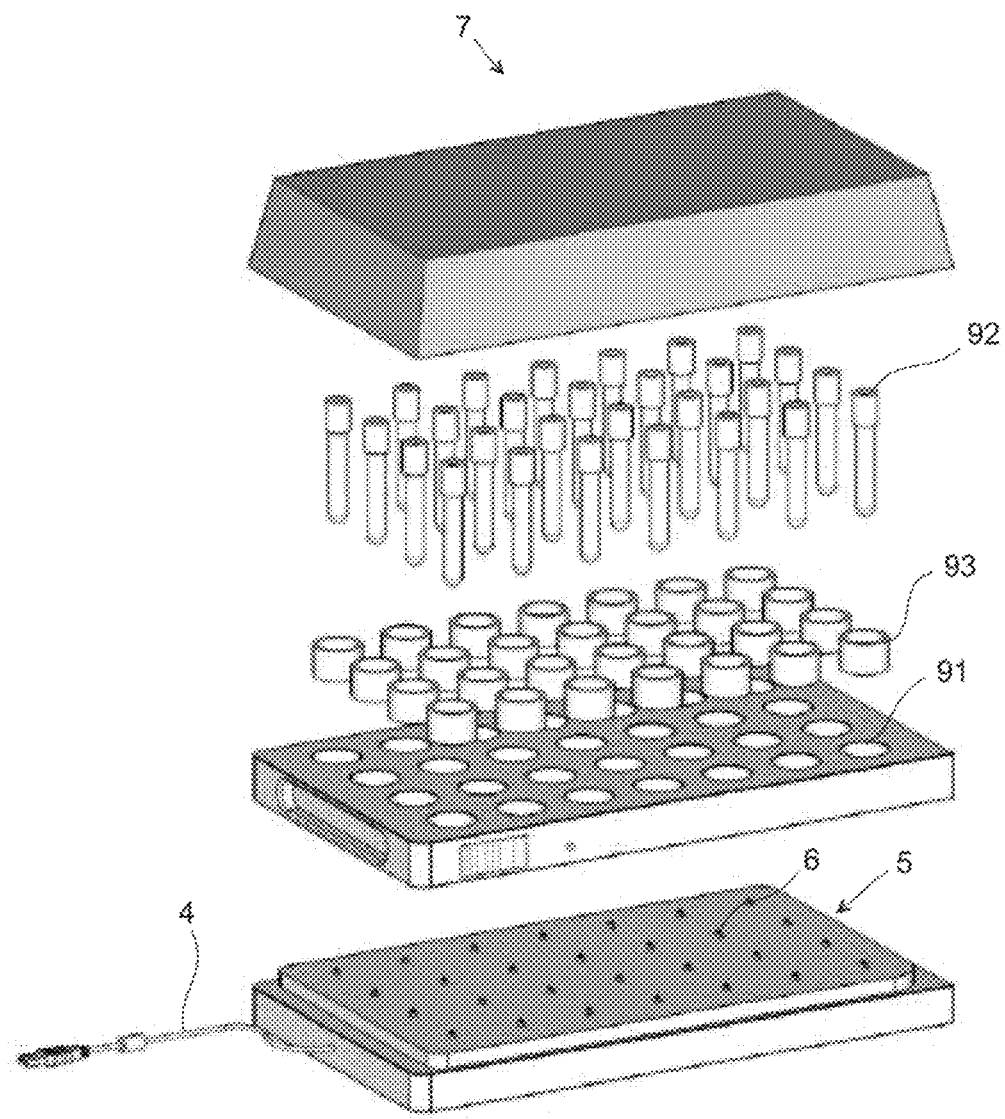
FIG. 3 shows parts of another apparatus according to the invention, separated from each other, in a slanted view from the side.

In many respects, the apparatus according to the invention can be implemented in a way different from the above-presented example embodiment. FIG. 3 shows another embodiment of the apparatus according to the invention, where the identification device 5 is similar to that in the embodiment of FIG. 1 but where the organizer 9 is implemented in a way different from the organizer according to the embodiment of FIG. 1 so that it is suitable for dispensing units 92 which are sample tubes, that is, which are intended for the collection and delivery of samples (for example, blood tests). The seats in the organizer of FIG. 3 comprise intermediate pieces 93, by which the sample tubes used as the dispensing units 92 can be kept in a suitable position in the organizer 9 so that their bottom is placed above the detecting members in the identification device 5. The intermediate pieces can also be made of a photoconductive material (e.g. glass or clear plastic) so that they conduct and/or reflect light onto the side surfaces of the dispensing units 93.

The use of the apparatus according to FIG. 3 for collecting samples is, in the main principles, the same as in the embodiment of FIG. 1. The collecting units for sample tubes of prior art are equipped with an identification tag (e.g. a label) which is not necessarily needed any longer, because right after taking the sample in a laboratory, the sample tubes are placed onto the seats 91 of the organizer 9, detected by the detecting members 6 of the identification device 5, from which they are easily found again at the stage of analysis by placing the organizer 9 on the identification device and by connecting the identification device 5 to a data processing device that contains the dispensing data.

Not only the organizer but also the other devices of the apparatus according to the invention can be implemented in a way different from the example embodiment presented above. For example, it is possible to use detecting members other than light emitting diodes in the identification device. The detecting members could be, for example, filament lamps or mechanical pins which pop up at the dispensing units, in which the dispensed medicines, vitamins or samples have to be dispensed or administered. In the embodiments of FIGS. 1 to 3, the organizer, the identification device and the dispensing units are made of plastic (e.g. by injection moulding), but it is also possible to use other materials, such as aluminium, wood, or stainless steel. Moreover, the shape of the organizer, the identification device and the lid can be different from the rectangular shape, for example polygonal (e.g. triangular, pentagonal or hexagonal), circular, or oval. However, these three parts are usually uniform in shape, wherein a maximum number of dispensing units, whose shape may also be different from the circular shape in the example embodiments, can be fitted on the organizer of the apparatus. Furthermore, for example the device for connecting the identification device, and the identification of the organizers can also be implemented in a different way. The connecting device may be another connecting cable than a USB cable or, for example a wireless connection, in which case, however, a separate power source is needed for the identification device, for example an accumulator, a battery, or a transformer. When an accumulator or a battery is used, the advantage is that the apparatus can be operated in a fully wireless manner. The identification of the organizers in the dispensing step can be performed, instead of bar code identification, by applying identification based on the RFID technology, or in such a way that both the identification tag 16 and the organizer tag 17 can be tags functioning by the bar code technique or another technique (e.g. hologram, or the like). Furthermore, it should be noted that as organizers in such an apparatus it is also possible to use such organizers which have a different number of seats than the number of detecting members in the identification device, wherein a seat is not always aligned at each detecting member when the organizer is placed in connection with the identification device. The invention is thus not limited to the above-presented example embodiments, but it may vary within the scope of protection determined by the claims.

The invention claimed is:

1. An apparatus for dispensing medicines, vitamins and/or samples, the apparatus comprising:
   an organizer,
   dispensing units for the medicines, vitamins and/or samples to be placed on the organizer, the organizer comprising seats in which the dispensing units can be placed, and
   an identification device without a data processing device and that enables a data processing device outside of the apparatus to control the apparatus through the identification device when the identification device is connected with the data processing device such that the data processing device can provide dispensing data on the medicines, vitamins and/or samples, wherein:
   the identification device comprises detecting members to be controlled to a detecting state by means of detecting signals to be generated on the basis of dispensing data in the data processing device,
   the identification device is separable from the organizer and is configured to be brought in connection with the organizer in such a way that at least some of the detecting members are aligned with at least some of the seats of the organizer,
   at least those dispensing units, which are aligned with at least one detecting member, can be identified by means of detecting signals generated on the basis of dispensing data in the data processing device, and
   the organizer comprises an organizer tag and the identification device comprises a reader device connected to the data processing device outside of the apparatus and configured to identify the organizer connected to the identification device on the basis of the organizer tag, when the organizer is placed in connection with the identification device and the identification device is connected to the data processing device.

2. The apparatus according to claim 1, wherein the detecting members are, in the detecting state, light emitting detecting members which are arranged to be set in the detecting state when they receive a detecting signal.

3. The apparatus according to claim 2, wherein each seat is provided with a maximum of one detecting member.

4. The apparatus according to claim 3, wherein the detecting members are configured to detect whether the seat is occupied by a separate dispensing unit or whether the seat is empty.

5. The apparatus according to claim 2, wherein the detecting members are light emitting diodes and that the detecting signal is an electric current that lights the light emitting diode.

6. The apparatus according to claim 5, wherein the seats in the organizer are openings formed in the organizer, and that the dispensing units are configured to be supported to the seats in such a way that they come above the detecting members of the identification device.

7. The apparatus according to claim 1, wherein
   the identification device is a plate-like or at least partly plate-like piece, from whose upper surface upwards protrude detecting members spaced from each other, and that the upper part of the identification device comprises an adapter part, in which the organizer can be fitted in such a way that the detecting members are aligned with the seats placed underneath them.

8. The apparatus according to claim 1, wherein the apparatus is equipped with a lid that can be locked.

* * * * *